United States Patent [19]

Ross et al.

[11] Patent Number: 5,569,235
[45] Date of Patent: Oct. 29, 1996

[54] VALVE AND VALVED CONTAINER FOR USE WITH A SYRINGE FITTING

[75] Inventors: James B. Ross, Livermore; Ronald Chang, Redwood City, both of Calif.

[73] Assignee: Modern Medical Devices, Fremont, Calif.

[21] Appl. No.: 263,790

[22] Filed: Jun. 21, 1994

[51] Int. Cl.⁶ .......................... A61M 5/00; A61M 19/00; F16K 51/00

[52] U.S. Cl. ................ 604/403; 251/149.1; 604/249

[58] Field of Search ............................ 604/403, 246, 604/249, 83, 86, 256, 409, 411; 251/342, 347, 349, 149.1, 149.4, 149.8, 149, 149.3

[56] References Cited

U.S. PATENT DOCUMENTS

| | | | |
|---|---|---|---|
| 2,859,932 | 11/1958 | Mackal | 251/349 |
| 4,190,048 | 2/1980 | Sampson | 604/249 |
| 5,242,393 | 9/1993 | Brimhall et al. | 604/249 |
| 5,423,791 | 7/1995 | Bartlett | 604/403 |

*Primary Examiner*—John G. Weiss
*Assistant Examiner*—David J. Cho
*Attorney, Agent, or Firm*—LeeAnn Gorthey; Peter J. Dehlinger

[57] ABSTRACT

A valve for a needleless syringe fitting is disclosed. The valve has a receptacle fitting for releasable attachment to the syringe fitting, a valve chamber, a valve seat adjacent the chamber, and elastomeric sealing bowl within the chamber. The bowl is deformed and partially inverted when the syringe fitting is attached to the receptacle fitting, causing the valve to open. Also disclosed is a valved container in which a vial is sealed by a valve of this type.

14 Claims, 4 Drawing Sheets

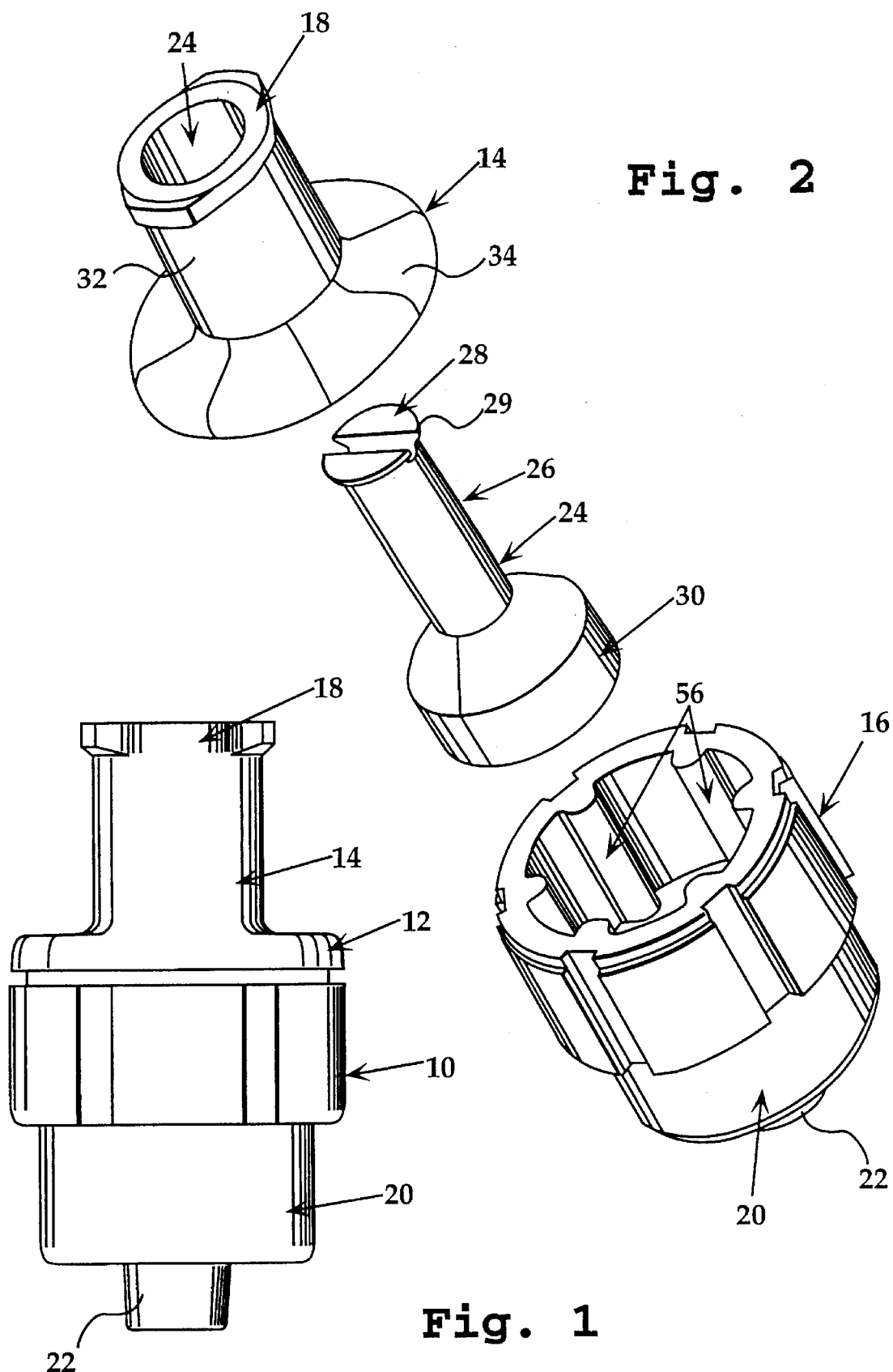

VALVE AND VALVED CONTAINER FOR USE WITH A SYRINGE FITTING

FIELD OF THE INVENTION

The present invention relates to a valve and valved container for use with a syringe fitting, such as "LEUR-LOK" male and female receptacle fittings, on a syringe or an intravenous line.

BACKGROUND OF THE INVENTION

A variety of syringe closure valves are employed in hospital and other medical/dental settings for use on intravenous lines employed for administering drugs, anesthetics, or nutritional supplements by IV route. The purpose of the closure valve is to block fluid flow out of the line, but allow fluid introduction into the line by a syringe connected to the valve.

The valve may be a simple membrane device having an elastomeric plug which can be penetrated by a needle, requiring that the syringe be equipped with a needle. The problem with this type of valve is the inconvenience and health risk of using a needle, and the problem of needle disposal.

An alternative type of valve is designed for use with a needleless syringe. With this type of valve, the needle fitting of the syringe is attached directly to the valve, forcing the valve into an open condition. Some valves of this type are once-only valves, i.e., not designed to return to a closed condition, or not able to effectively return to a closed condition, after the syringe is removed. In particular, the valve may be leaky to back flow in a closed condition after one or a few uses.

Needleless valves known in the prior art also tend to be damaged or destroyed if the user inadvertently attempts to operate the valve by needle puncture. Further, needleless syringe valves may be expensive in manufacture and construction, due to the number of valve parts involved.

It would thus be desirable to provide a syringe valve that can be operated repeatedly and effectively with a needleless syringe, but which functions without damage if a user attempts to operate the valve with a needle, and which has a simple, easily manufactured construction.

Such a valve would also be useful in a valved container for supplying a medicament or the like in liquid or lyophilized form. Here a needleless syringe could be employed to introduce liquid into the vial, in the case of dehydrated vial contents, and to remove a desired amount of liquid contents from the vial. At the same time, the valve would function normally and without damage if a needle were inadvertently used to operate the valve.

SUMMARY OF THE INVENTION

The invention includes, in one aspect, a valve for use with a syringe fitting, such as a male LEUR-LOK™ fitting receptacle, having an extended neck. The valve includes a housing that defines an elongate bore terminating at an outer end in a receptacle fitting adapted to releasably engage the syringe fitting, with the neck of the syringe fitting being received in an outer end region of the bore. Also formed by the housing are a valve chamber communicating with the bore, a valve seat formed between the bore and chamber, and a chamber opening.

A valve plunger in the valve has an elastomeric bowl disposed in the chamber for movement between a relaxed condition, in which the bowl is in sealing engagement with the valve seat, and a partially inverted condition, in which the bowl is separated from the valve seat. The bowl is connected to a plunger stem which extends into the outer end region of the bore.

When a syringe fitting is attached to the valve's receptacle fitting, insertion of the syringe fitting neck into the valve bore's outer end region forces the plunger stem toward the valve chamber, moving the plunger bowl from its relaxed to its partially inverted condition, opening the valve to fluid flow between the valve seat and bowl. Removing the syringe from the valve causes the bowl to return to its relaxed condition, closing the valve.

The plunger is preferably formed as a unitary, elastomeric piece that may be penetrated with a needle, allowing valve operation by a syringe equipped with a needle.

Also in a preferred embodiment, the plunger bowl defines an interior space that communicates with the valve opening, such that applying pressure to the valve from the opening side of the valve, with the valve in a closed condition, acts to press the bowl against the valve seat, to maintain the valve in its closed condition.

In one general embodiment, for use as an inline valve, the valve housing also forms a syringe fitting at the end of the valve opposite the receptacle fitting. The syringe fitting has an extended neck defining a second bore that serves as the opening of the chamber.

This embodiment of the valve may be constructed of (i) a head piece forming the valve's receptacle fitting, the first-mentioned bore, and the valve seat, and (i) a base piece forming the valve chamber, the syringe fitting, and the valve opening.

In another general embodiment, for use with a vial having an opening, the housing is attached to the vial with the valve opening communicating with the vial opening. In this embodiment, the valve housing is composed of (i) a head piece forming the receptacle fitting, the first-mentioned bore, and said valve seat, and (ii) a base piece formed integrally with the vial and forming the valve chamber.

In another aspect, the invention includes a valved storage container for storing medicaments or the like, for delivery of the container contents by a syringe of the type equipped with a syringe fitting having a neck. The container includes (1) a vial having an opening, and (2) a valve of the type described above attached to vial.

These and other objects and features of the invention will become more fully apparent when the following detailed description of the invention is read in conjunction with the accompanying drawings.

BRIEF DESCRIPTION OF THE DRAWINGS

FIG. 1 is a side view of a valve constructed in accordance with the invention;

FIG. 2 is an exploded view of the valve, showing its three-piece construction;

DETAILED DESCRIPTION OF THE INVENTION

I. Syringe Valve

Figure 3A:
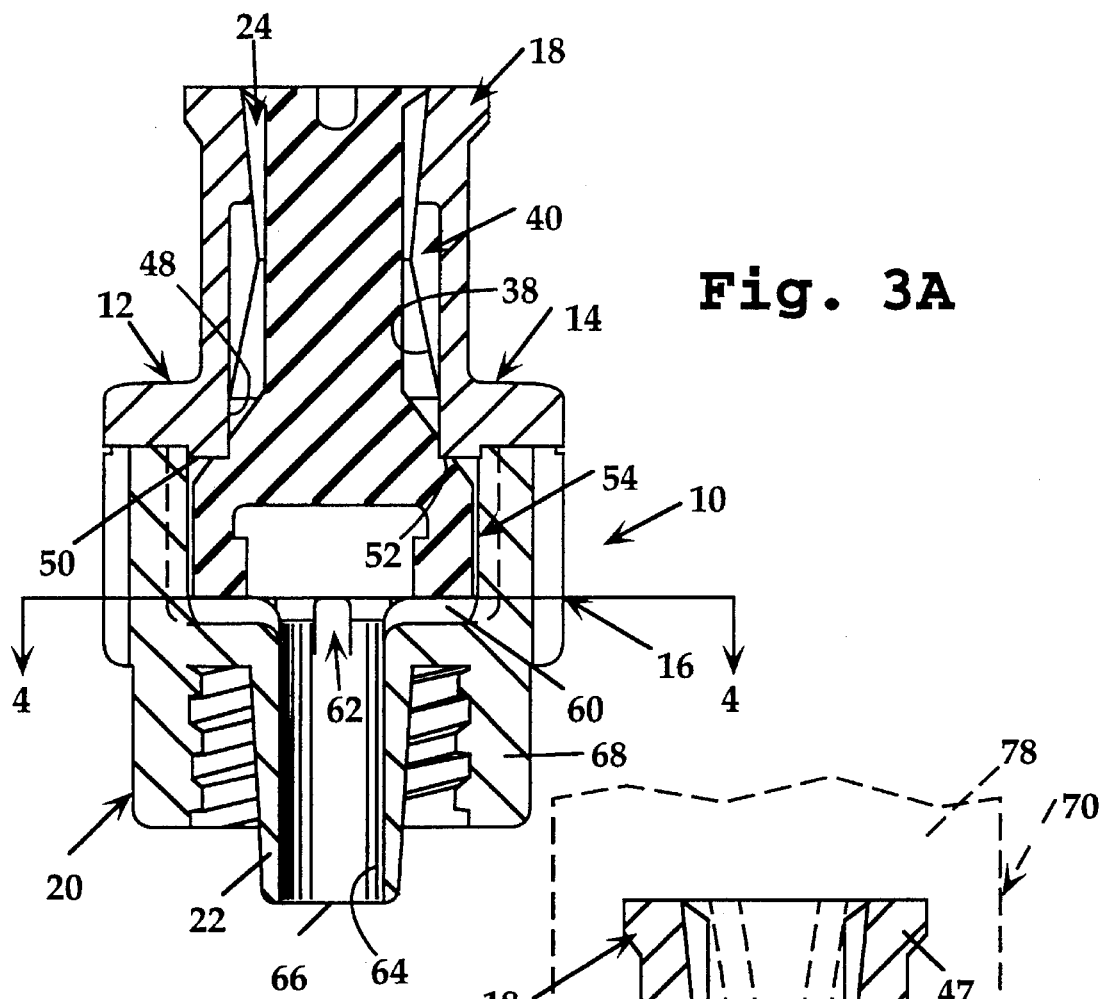
FIGS. 3A and 3B sectional views of the valve taken along the flow axis of the valve, showing the valve in a closed condition (FIG. 3A), and an open condition produced by attachment of a syringe fitting to the valve (FIG. 3B)

FIG. 1 shows in side view, a valve 10 constructed in accordance with one embodiment of the invention. The valve has a two-piece housing 12 composed of a head piece 14 and a base piece 16, seen in exploded view in FIG. 2. The head piece forms a LEUR-LOK™ receptacle fitting 18 which is adapted to releasably engage a syringe fitting, as described below. The base piece forms a complementary LEUR-LOK™ syringe fitting 20 having an extended neck 22, and is adapted to releasably engage a receptacle fitting of the type formed by the valve's head piece. Thus, the valve provides both the female and male fittings required for releasable in-line attachment between a syringe and a feed line, or for coupling two sides of a feed line.

The valve is operated between open and closed conditions by an elastomeric plunger 24 seen in FIG. 2. The plunger includes an elongate stem 26 terminating at a grooved end 28 which has a seal or wiper 29 for preventing liquid entry into the valve from the receptacle fitting. The stem is attached to a bowl 30 designed to be moved between a relaxed condition, as shown in FIGS. 2 and 3A, in which the interior of the bowl is generally concave (see FIG. 3A), and a deformed, partially inverted condition (see FIG. 3B) in which the central portion of the bowl is inverted, i.e., partially or completely filled.

Figure 3B:
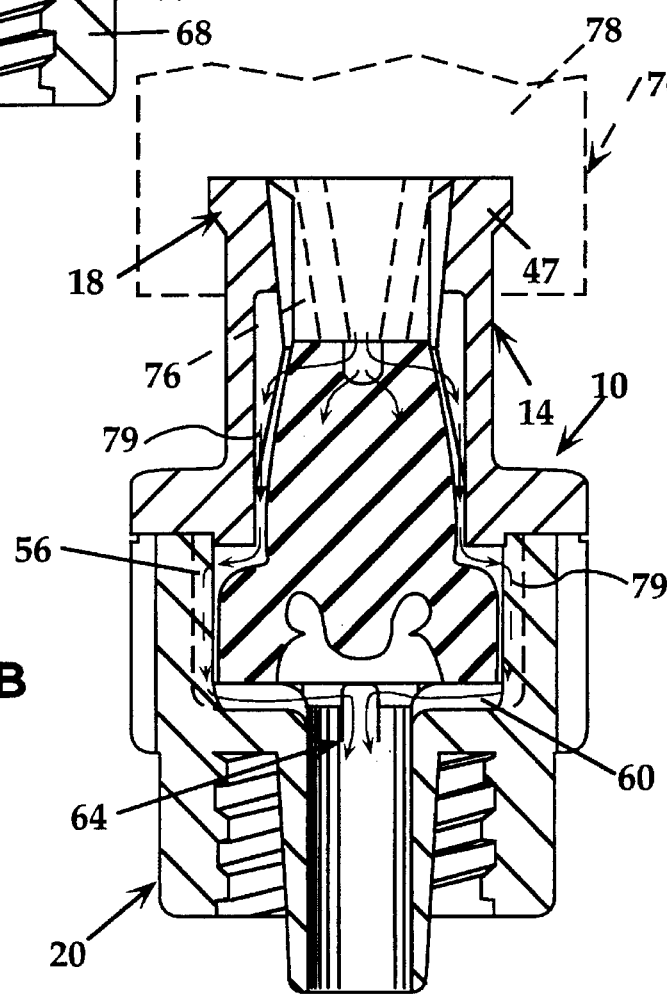

Details of the head piece construction can be seen in FIGS. 2, and 3A and 3B. The piece includes a chimney 32 and a skirt 34. As seen best in FIGS. 3A and 3B, the chimney defines an elongate bore having a plurality of shallow, V-shaped ribs, such as seen at 38, and intervening recesses, such as recess 40. The outer end region of the bore, corresponding roughly to the inwardly tapered section of ribs 38, is dimensioned to receive therein, the neck of a syringe fitting, such as neck 76 or fitting 70, as shown in FIG. 3B. The bore terminates at its outer end in receptacle fitting 18, forming one of the valve ports. The fitting has a lip 47 for threadedly engaging the syringe fitting, as seen in FIG. 3B.

An annular wall portion 48 at the inner end of the bore intersects an annular ring portion 50 of the head piece to form, at their orthogonal intersection, an annular valve seat 52.

The construction of the base piece can be seen with reference to FIGS. 2, 3A and 3B, and 4. The portion of the base piece that adjoins the head piece defines a valve chamber 54 for the plunger bowl. As seen best in FIG. 2, the wall of the valve chamber has a plurality of axially disposed ribs, such as ribs 56, which act to space the plunger from the chamber side wall.

Figure 4:
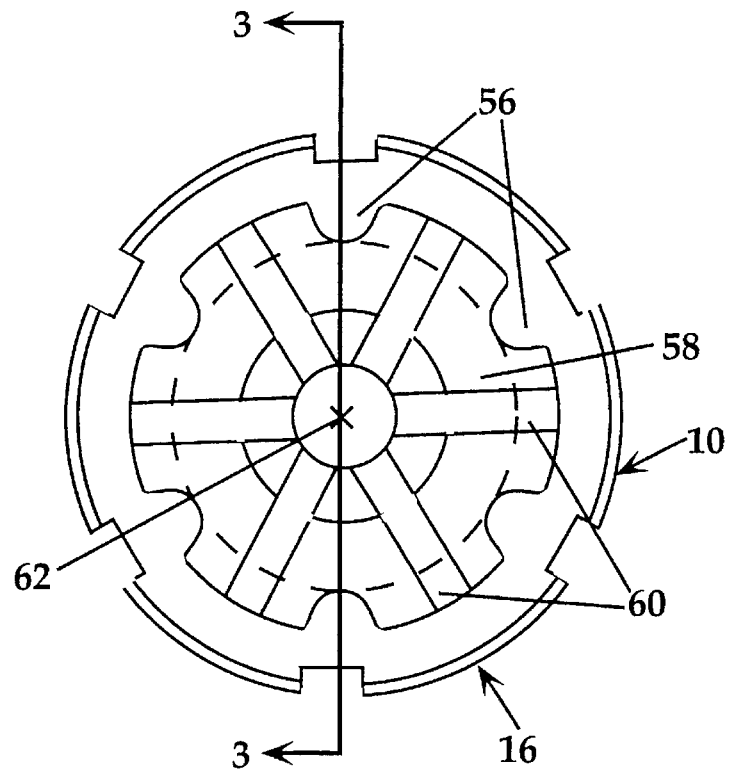
FIG. 4 is a sectional view of the valve taken through line 4—4 in FIG. 2.

The bottom wall of the chamber, seen at 58 in FIG. 4, is likewise provided with a plurality of ribs, such as ribs 60, which act to space the plunger bowl from the bottom wall. The central portion of the bottom wall has a central opening 62.

As mentioned above, and with reference to FIGS. 3A and 3B, the lower portion of the base piece forms a syringe fitting 20 having a neck 22 for engaging a receptacle fitting of the type described above. Neck 22 defines an internal bore 64 which extends from opening 62 to a lower valve port 66. The fitting also includes a threaded sleeve 68 used for threadedly engaging the lip (similar to lip 47) of a receptacle fitting.

The head and base pieces can be formed as molded polymeric articles, by standard polymer molding techniques. The plunger is formed as a unitary elastomer article, preferably from a soft rubber or silicone material, accordingly to known molding methods. One preferred material is liquid silicone rubber, such as cured Q74850 silicon rubber supplied in uncured form by Dow Chemical Co. (Midland, Mich.). The valve is assembled, as seen in FIG. 2, by inserting the plunger bowl into the valve chamber of the base piece, and pressing, gluing or ultrasonically welding the head piece onto the base piece, with the plunger stem received in the bore of the head piece.

The operation of the device will be described with respect to valve coupling to a syringe, it being understood that other devices, such as an in-line connector, equipped with a syringe fitting may be employed.

Figure 5:
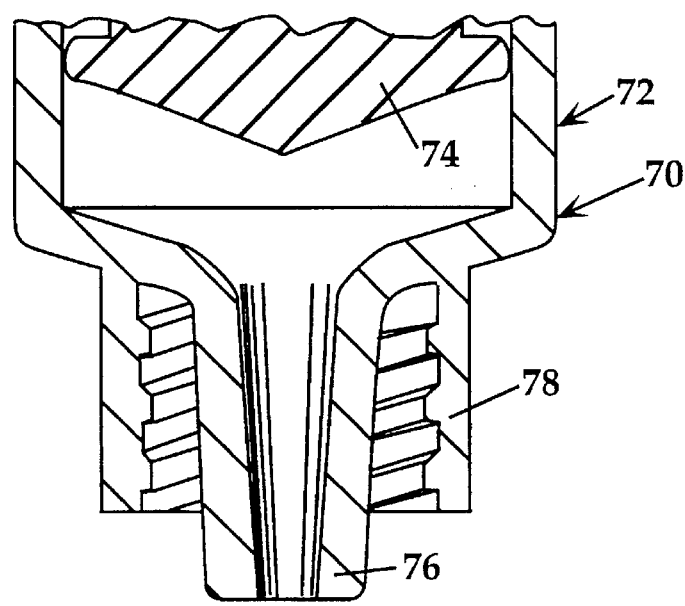
FIG. 5 is a sectional view of a lower portion of a syringe having a fitting of the type that can be releasably attached to the valve.

FIG. 5 shows a lower end portion of a syringe 70 for use with the valve. The syringe has a barrel 72 with a plunger 74. The barrel tapers to a neck 76 forming part of the syringe fitting. Also forming part of the fitting is a threaded sleeve 78 for threadedly engaging the lip of a receptacle fitting, such as fitting 18 in valve 10.

FIG. 3B illustrates how engagement of the syringe fitting with the valve operates to open the valve. The figure shows the disposition of the neck of a syringe, such as neck 76 of syringe 70, when the syringe fitting is releasably attached to the valve.

Prior to attaching a syringe fitting to the valve, the upper surface of the bowl in the valve chamber is pressed against the valve seal, forming an leak-tight valve seal, as shown in FIG. 3A. Applying fluid pressure to the valve, from the lower side of the valve in the figure, when the valve is in a closed condition, acts to force the bowl against the seal, to maintain the valve in a closed condition even under pressure.

When a syringe fitting is releasably attached to the valve, the neck of the fitting, such as neck 76 in syringe 70 forces the plunger stem toward the valve chamber, as illustrated in FIG. 3B, causing the bowl to deform to a partially inverted shape in which the upper surface of the bowl is spaced from the valve seal. Fluid may now flow through the valve, in either direction, across the valve seat. In particular, the fluid introduced from the receptacle side of the valve will flow into the barrel recesses, such as recess 40, across the valve seat, down the recesses formed between the side and bottom ribs, such as ribs 56, 60, respectively in the valve chamber, and out bore 64 as shown by arrows 79, with fluid drawn into the valve from the syringe fitting side traveling the same pathway in the reverse direction. When the syringe is removed, the elastomeric plunger returns to its original shape, closing the valve.

From the foregoing, it will also be appreciated how various objects of the invention are met. Because of the elasticity of the plunger, the valve may be opened and closed repeatedly by syringe attachment and release without degrading valve performance.

The valve will function for valving even if the syringe fitting coupled to valve inadvertently carries a needle. In this event, the needle will merely penetrate the elastomeric plunger, without damage to the plunger or other valve components, providing a direct fluid conduit between opposite sides of the valve. After the desired fluid flow through the valve, the needle is removed, and the elastomeric plunger assumes its original shape and function.

The valve is simple in construction and manufacture, requiring assembly of three simple molded parts, with attachment of the head and base pieces by ultrasonic weld, press fit, or glue.

II. Valved Container

Figure 6:
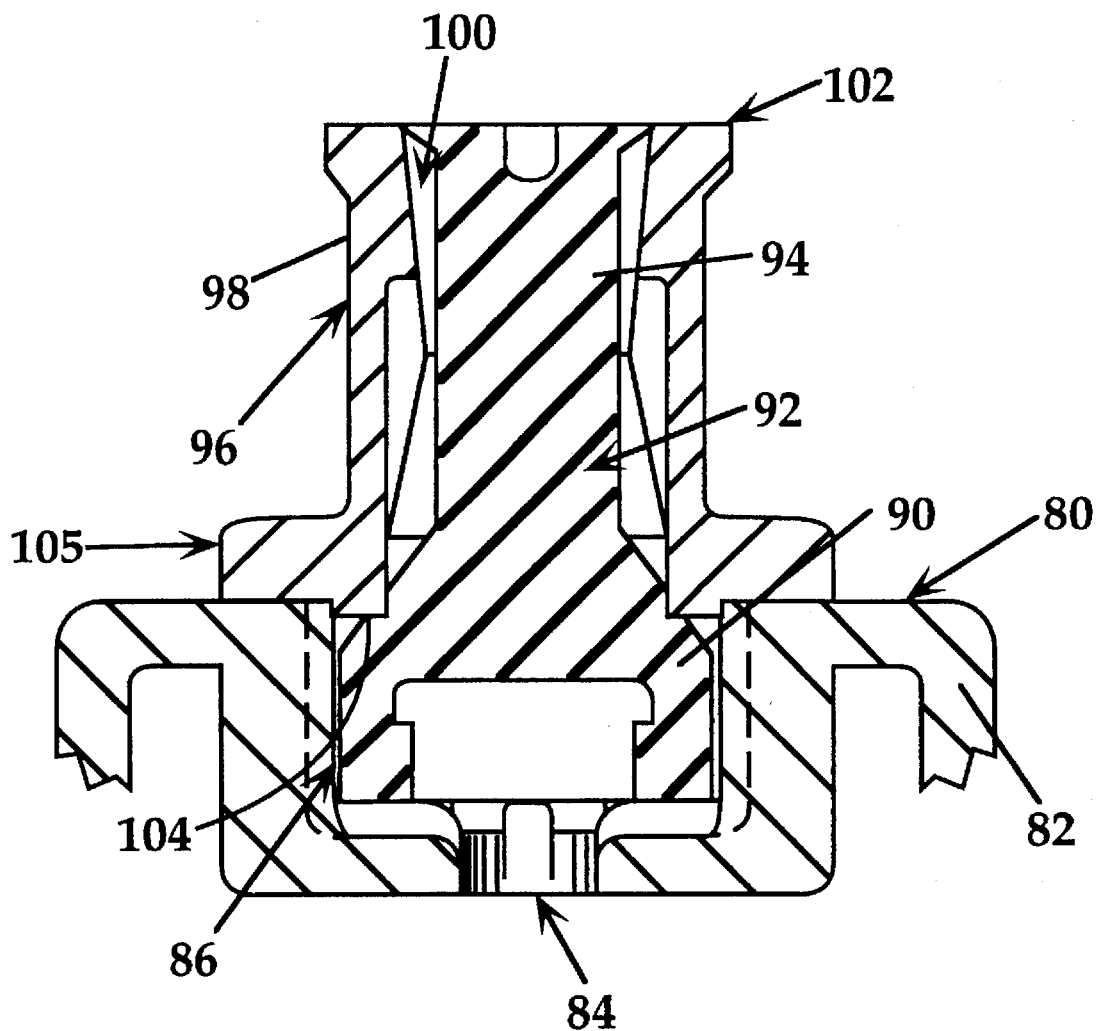
FIG. 6 is a sectional view of a valved container formed in accordance with another embodiment of the invention.

In another aspect, the invention includes a valved storage container for storing a medicament or the like. The container, shown fragmentarily at 80 in FIG. 6, is intended to maintain the container contents in a sealed condition, and allow introduction of liquid into the container, and/or removal of liquid from the container by releasable attachment of a syringe fitting to the container valve.

Container 80 includes a vial 82, typically a glass or polymer vial, having an opening 84. The opening communicates with a valve chamber 86 which has the same general construction as the valve chamber described above with respect to valve 10 in FIG. 1, but which is preferably formed integrally with the vial. Specifically, the valve chamber houses the bowl 90 of a plunger 92, with ribs formed on the side and lower walls of the chamber acting to space a bowl from the chamber walls, when the valve is in its closed condition (as shown), and to maintain a fluid-flow space along the side and bottom walls when the bowl is in its deformed, partially inverted condition, providing a fluid passageway through the valve.

Plunger 92 in the container has the same general construction as plunger 24 in valve 10, and includes a neck 94 and bowl 90, preferably formed as a unitary elastomeric article.

Also forming part of the valve is a head piece 96 having the same general construction as head piece 14 in valve 10. Specifically head piece 96 (i) has a chimney 98 defining an internal bore 100, for receiving plunger neck 94, (ii) terminates at a receptacle fitting 102 at the outer end of the bore, and (iii) defines a valve seat 104 at the inner end of the bore. The head piece, and the portion of the vial forming the valve chamber collectively form a valve housing, indicated generally at 105.

In the closed condition of the valve, plunger 92 has the conformation shown in the figure, where the upper surface of the bowl bites into the valve seal to maintain the valve in a closed condition. When a syringe fitting is releasably attached to the valve, the plunger is deformed, as illustrated in FIG. 3B, to deform and partially invert the plunger bowl, opening the space between and bowl and valve seat to provide a fluid passageway through the valve.

With the valve thus opened, liquid can be introduced into and/or removed from the vial by the needleless syringe. At the same time, the valve may be operated without damage if the syringe fitting is inadvertently equipped with a needle.

The valved container shares the advantages of valve 10 discussed above. The valve may be opened and closed repeatedly, by releasably attaching and removing a syringe fitting, without degradation of valve. The valve can be used with either a needleless or needle-bearing syringe fitting. The latter feature may be useful, for example, where it is desired to introduce liquid into the vial to dissolve a lyophilized medicament, store the container in a sealed condition, and withdraw solution from the vial from a syringe with needle. The container is easily constructed, simply by attachment of a head piece to the vial opening, with the plunger captured between the two.

Although the invention has been described with reference to particular embodiments and operations, it will be appreciated that various changes and modification may be made without departing from the invention.

It is claimed:

1. A valve for use with a syringe fitting having an extended neck, said valve comprising (a) a housing defining (i) an elongate bore terminating at an outer end in a receptacle fitting adapted to releasably engage the syringe fitting, with the neck thereof received in an outer end region of the bore, (ii) a valve chamber communicating with the bore, (iii) a valve seat formed between said bore and chamber, and (iv) a chamber opening, and (b) a valve plunger having (i) an invertable elastomeric bowl defining an open interior region, disposed in said chamber for movement between a relaxed condition, in which the bowl is in sealing engagement with the valve seat, and a partially inverted condition, in which the open interior of the bowl is at least partially filled, and the bowl is separated from the valve seat, and (ii) a stem connected to the bowl and extending into the outer end region of the bore, wherein attaching a syringe fitting to the valve, with insertion of the syringe-fitting neck into the valve bore's outer end region, forces the plunger stem toward said valve chamber, moving the invertable plunger bowl from its relaxed to its partially inverted condition, opening the valve to fluid flow around the plunger stem and between the valve seat and bowl, and removing the syringe fitting the valve causes the bowl to return to its relaxed condition, closing the valve.

2. The valve of claim 1, wherein the stem and bowl in the plunger are formed as a unitary elastomeric plunger.

3. The valve of claim 2, wherein the plunger may be penetrated with a needle.

4. The valve of claim 1, wherein said plunger bowl defines an interior space that communicates with said opening, such that applying pressure to the valve from the opening side of the valve, with the valve in a closed condition, acts to press the bowl against the valve seat, to maintain the valve in its closed condition.

5. The valve of claim 1, wherein said chamber opening is formed by a bore extending through a portion of the housing, and this housing portion forms an extended neck of a syringe fitting opposite said receptacle fitting in the valve.

6. The valve of claim 5, wherein the receptacle and syringe fittings in the valve are complementary male and female fittings.

7. The valve of claim 4, wherein said valve housing is composed of (i) a head piece forming said receptacle fitting, the first-mentioned bore, and said valve seat, and (i) a base piece forming said valve chamber, the syringe fitting, and said opening.

8. The valve of claim 1, for use with a vial having an opening, wherein said housing is attached to said vial with the valve chamber opening in communication with the vial opening.

9. A valved storage container for storing medicaments or the like, for delivery of the container contents by a syringe of the type equipped with a male fitting having a neck, said container comprising (1) a vial having an opening, and (2) a valve attached to the vial, said valve formed of (a) a housing defining (i) an elongate bore terminating at an outer end in a receptacle fitting adapted to releasably engage the syringe fitting, with the neck thereof received in an outer end region of the bore, (ii) a valve chamber communicating with the bore, (iii) a valve seat formed between said bore and chamber, and (iv) a chamber opening, and (b) a valve plunger having (i) an invertable elastomeric bowl defining an open interior region, disposed in said chamber for movement between a relaxed condition, in which the bowl is in sealing engagement with the valve seat, and a partially inverted condition, in which the open interior of the bowl is at least partially filled, and the bowl is separated from the valve seat, and (ii) a stem connected to the bowl and extending into the outer end region of the bore, wherein attaching a syringe fitting to the valve, with insertion of the syringe-fitting neck into the valve bore's outer end region, forces the plunger stem toward said valve chamber, moving the invertable plunger bowl from its relaxed to its partially inverted condition, opening the valve to fluid flow around the plunger stem and between the valve seat and bowl, and removing the syringe fitting the valve causes the bowl to return to its relaxed condition, closing the valve.

10. The container of claim 9, wherein the stem and bowl in the plunger are formed as a unitary elastomeric plunger, and the plunger may be penetrated with a needle.

11. The container of claim 9, wherein said plunger bowl defines an interior space that communicates with said opening, such that fluid pressure within the vial, with the valve in a closed condition, acts to press the bowl against the valve seat, to maintain the valve in its closed condition.

12. The container of claim 9, wherein said valve housing is composed of (i) a head piece forming said receptacle fitting, the first-mentioned bore, and said valve seat, and (i) a base piece forming said valve chamber, and said opening.

13. The container of claim 12, wherein said base piece is formed integrally with the vial.

14. The container of claim 12, wherein the stem and bowl in the plunger are formed as a unitary elastomeric plunger, and the plunger may be penetrated with a needle.

* * * * *